(12) United States Patent
Kawahara

(10) Patent No.: US 10,633,570 B2
(45) Date of Patent: Apr. 28, 2020

(54) ANTI-ICE NUCLEATION ACTIVATOR

(71) Applicants: THE SCHOOL CORPORATION KANSAI UNIVERSITY, Suita-shi, Osaka (JP); SHIN NIPPON YAKUGYO CO., LTD., Tokyo (JP)

(72) Inventor: Hidehisa Kawahara, Suita (JP)

(73) Assignees: THE SCHOOL CORPORATION KANSAI UNIVERSITY, Osaka (JP); SHIN NIPPON YAKUGYO CO., LTD., Tokyo (JP)

( * ) Notice: Subject to any disclaimer, the term of this patent is extended or adjusted under 35 U.S.C. 154(b) by 79 days.

(21) Appl. No.: 15/566,893

(22) PCT Filed: Apr. 13, 2016

(86) PCT No.: PCT/JP2016/061904
§ 371 (c)(1),
(2) Date: Oct. 16, 2017

(87) PCT Pub. No.: WO2016/167284
PCT Pub. Date: Oct. 20, 2016

(65) Prior Publication Data
US 2018/0127631 A1 May 10, 2018

(30) Foreign Application Priority Data
Apr. 16, 2015 (JP) ................... 2015-084586

(51) Int. Cl.
*C09K 5/20* (2006.01)
*A23L 3/37* (2006.01)
(Continued)

(52) U.S. Cl.
CPC .............. *C09K 5/20* (2013.01); *A01N 1/0221* (2013.01); *A23B 4/09* (2013.01); *A23B 7/055* (2013.01);
(Continued)

(58) Field of Classification Search
CPC ............. C09K 5/20; C09K 5/08; C09K 5/006
(Continued)

(56) References Cited

U.S. PATENT DOCUMENTS 4,803,080 A * 2/1989 Benedikt ................ A61K 31/52
424/475
6,355,726 B1 * 3/2002 Doemling ............. C07C 291/10
436/528
(Continued)

FOREIGN PATENT DOCUMENTS

CN 103539536 A 1/2014
CN 104094924 A 10/2014
(Continued)

OTHER PUBLICATIONS

Tagawa et al. "Anti-Ice Nucleation Activities of Adenine and Poly-A Nucleotides", Biocontrol Science, 2017, vol. 22, No. 4, 233-237 (Year: 2017).*

(Continued)

*Primary Examiner* — Jane L Stanley
(74) *Attorney, Agent, or Firm* — MH2 Technology Law Group, LLP

(57) ABSTRACT

Disclosed are an anti-ice nucleation activator comprising a purine base or a purine base-containing polymer, and an antifreeze liquid comprising the anti-ice nucleation activator and water; a method for improving the anti-ice nucleation activity of a biological material, the method comprising bringing the anti-ice nucleation activator into contact with the biological material; and a method for preserving a biological material, the method comprising bringing the anti-ice nucleation activator into contact with a biological material.

4 Claims, 2 Drawing Sheets

(51) Int. Cl.
*C09K 3/18* (2006.01)
*C07D 473/08* (2006.01)
*A23L 3/375* (2006.01)
*C07D 473/10* (2006.01)
*A61K 31/52* (2006.01)
*A23L 2/52* (2006.01)
*A23B 4/09* (2006.01)
*A01N 1/02* (2006.01)
*C07D 473/02* (2006.01)
*A23L 2/42* (2006.01)
*A61K 31/522* (2006.01)
*C07D 473/04* (2006.01)
*C07D 473/18* (2006.01)
*A23L 2/44* (2006.01)
*C07D 473/30* (2006.01)
*A23B 7/055* (2006.01)
*C07D 473/34* (2006.01)
*C07D 473/12* (2006.01)
*C07D 473/00* (2006.01)

(52) U.S. Cl.
CPC .......... *A23L 2/42* (2013.01); *A23L 2/44* (2013.01); *A23L 2/52* (2013.01); *A23L 3/37* (2013.01); *A23L 3/375* (2013.01); *A61K 31/52* (2013.01); *A61K 31/522* (2013.01); *C07D 473/00* (2013.01); *C07D 473/02* (2013.01); *C07D 473/04* (2013.01); *C07D 473/08* (2013.01); *C07D 473/10* (2013.01); *C07D 473/12* (2013.01); *C07D 473/18* (2013.01); *C07D 473/30* (2013.01); *C07D 473/34* (2013.01); *C09K 3/18* (2013.01)

(58) Field of Classification Search
USPC .......................................................... 252/71
See application file for complete search history.

(56) References Cited

U.S. PATENT DOCUMENTS

| | | | |
|---|---|---|---|
| 6,485,959 | B1 | 11/2002 | Demetriou et al. |
| 2003/0111638 | A1* | 6/2003 | Fahy ........................ A01N 1/02 252/70 |
| 2004/0034195 | A1* | 2/2004 | Nishimiya ............ C07K 14/461 530/350 |
| 2005/0019917 | A1* | 1/2005 | Toledo-Pereyra ....... A01N 1/02 435/375 |
| 2005/0161631 | A1* | 7/2005 | Walker ...................... C10L 3/06 252/70 |
| 2010/0312045 | A1* | 12/2010 | Ramlov ................... A01N 1/02 600/35 |
| 2011/0183021 | A1* | 7/2011 | Daly .................. A61K 31/7076 424/780 |
| 2013/0146803 | A1* | 6/2013 | Kawahara ............ A01N 1/0221 252/70 |
| 2013/0165626 | A1* | 6/2013 | Fukuoka ................ C09K 3/185 530/324 |
| 2014/0326923 | A1 | 11/2014 | Miller et al. |

FOREIGN PATENT DOCUMENTS

| | | | | |
|---|---|---|---|---|
| EP | 1644481 | A1 | 4/2006 | |
| JP | S58-070828 | A | 4/1983 | |
| JP | S62-234022 | A | 10/1987 | |
| JP | 2000-063814 | A1 | 2/2000 | |
| JP | 2006-524260 | A | 10/2006 | |
| JP | 2011-504107 | A | 2/2011 | |
| JP | 2015-038170 | A | 2/2015 | |
| RU | 1434729 | A1 * | 1/1998 | ............ C08F 291/00 |
| WO | 2004/093658 | A | 11/2004 | |
| WO | 2005/003327 | A1 | 1/2005 | |

OTHER PUBLICATIONS

Chupov et al. SU 1434729 A1, English abstract, published Jan. 10, 1998 (Year: 1998).*
International Search Report dated Jul. 19, 2016 from International Application No. PCT/JP2016/061904, 5 pages with English tranlsation.
Kawahara et al., "Identification of a Compound in Spices Inhibiting the Ice-nucleating Activity of Erwinia uredovora KUIN-3", Journal of Antibacterial and Antifungal Agents, 1996, vol. 24, No. 2, pp. 95-100.
Yamashita et al., "Identification of a Novel Anti-ice-nucleating Polysaccharide from Bacillus thuringiensis YY529", Biosci. Biotechnol. Biochem., 2002, vol. 66, No. 5, pp. 948-954.
Extended European Search Report dated Feb. 14, 2019 from European Application No. 16780075.4, 11 pages.

* cited by examiner

ANTI-ICE NUCLEATION ACTIVATOR

CROSS-REFERENCE TO RELATED APPLICATIONS

This application is a U.S. National Stage application of PCT/JP2016/061904 filed 13 Apr. 2016, which claims priority to Japanese Application No. 2015-084586 filed 16 Apr. 2015, the entire disclosures of which are hereby incorporated by reference in their entireties.

TECHNICAL FIELD

The present invention relates to an anti-ice nucleation activator and an antifreeze liquid. The present invention further relates to a method for improving the anti-ice nucleation activity of a biological material, and a method for preserving a biological material.

BACKGROUND ART

Since foreign substances contained in water form ice nuclei, water solidifies at 0° C. Such foreign substances are called ice nucleation active substances. Typical examples of known ice nucleation active substances include bacteria of the *Pseudomonas* genus, silver iodide, and the like. In contrast, pure water contains no foreign substances; therefore, ice nucleation does not occur. Even if pure water is cooled to a temperature lower than the freezing point (0° C.), for example, −39° C., pure water may not solidify (solidification). This is generally called "supercooling phenomenon."

Some anti-ice nucleation activators (supercooling accelerators), which promote the supercooling phenomenon, have previously been reported. The anti-ice nucleation activators are capable of forming water that does not freeze even at a temperature under the freezing point. As a result, expansion upon freezing does not occur, which allows cells of plants or animals to be preserved without being destroyed. Even if it is frozen once, only fine ice nuclei are formed, resulting in the occurrence of fine ice crystal formation. Thus, the application of anti-ice nucleation activators to the fields of food, biomaterials (organ preservation), etc., is expected.

For example, low-molecular-weight compounds, such as eugenol, which is a component of a spice (see Non-Patent Literature (NPL) 1); as well as high-molecular-weight compounds, such as polysaccharide from *Bacillus thuringiensis* (see NPL 2), have been reported to exhibit anti-ice nucleation activity.

However, although these anti-ice nucleation activators exhibit anti-ice nucleation activity towards bacteria, such as *Pseudomonas fluorescens*, which is an ice nucleation active substance, they exhibit low anti-ice nucleation activity towards silver iodide. Moreover, due to safety issues, the use of the anti-ice nucleation activators was difficult in the fields of food, biomaterials, etc.

CITATION LIST

Non-Patent Literature

NPL 1: H. Kawahara et al., J. Antibact. Antifung. Agents, 1996, Vol. 24, pp. 95-100

NPL 2: Y. Yamashita et al., Biosci. Biotech. Biochem., 2002, Vol. 66, pp. 948-954

SUMMARY OF INVENTION

Technical Problem

An object of the present invention is to provide an anti-ice nucleation activator and antifreeze liquid that exhibit anti-ice nucleation activity widely towards ice nucleation active substances, and that are applicable to the fields of food, biological materials, etc. Another object of the present invention is to provide a method for improving the anti-ice nucleation activity of a biological material using the anti-ice nucleation activator, and a method for preserving a biological material using the anti-ice nucleation activator.

Solution to Problem

In order to achieve the above objects, the present inventor conducted extensive research, and found that a purine base and a purine base-containing polymer are capable of achieving the above objects. The present invention has thus been accomplished.

More specifically, the present invention provides the following anti-ice nucleation activator, antifreeze liquid, and the like.

Item 1. An anti-ice nucleation activator comprising a purine base or a purine base-containing polymer.

Item 2. The anti-ice nucleation activator according to Item 1, wherein the purine base is at least one compound selected from the group consisting of adenine, purine, guanine, hypoxanthine, xanthine, theobromine, caffeine, uric acid, isoguanine, and theophylline.

Item 3. The anti-ice nucleation activator according to Item 1 or 2, wherein the purine base is adenine, uric acid, or caffeine.

Item 4. An antifreeze liquid comprising the anti-ice nucleation activator of any one of Items 1 to 3, and water.

Item 5. The antifreeze liquid according to Item 4, comprising the anti-ice nucleation activator in an amount of 0.1 to 10 mg/mL.

Item 6. A method for improving the anti-ice nucleation activity of a biological material, the method comprising the step of bringing the anti-ice nucleation activator of any one of Items 1 to 3 into contact with a biological material.

Item 7. A method for improving the anti-ice nucleation activity of food, the method comprising the step of bringing the anti-ice nucleation activator of any one of Items 1 to 3 into contact with food.

Item 8. A method for preserving a biological material, the method comprising the step of bringing the anti-ice nucleation activator of any one of Items 1 to 3 into contact with a biological material.

Item 9. A method for preserving food, the method comprising the step of bringing the anti-ice nucleation activator of any one of Items 1 to 3 into contact with food.

Item 10. Use of a purine base or a purine base-containing polymer as an anti-ice nucleation activator.

Advantageous Effects of Invention

The present invention provides an anti-ice nucleation activator and antifreeze liquid that exhibit anti-ice nucleation activity widely towards ice nucleation active substances, and that are applicable to the fields of food, biological materials, etc. The use of the anti-ice nucleation activator of the present invention is expected to enable long-term, low-temperature preservation of food, biological materials, etc.

DESCRIPTION OF EMBODIMENTS

1. Anti-Ice Nucleation Activator

Figure 1:
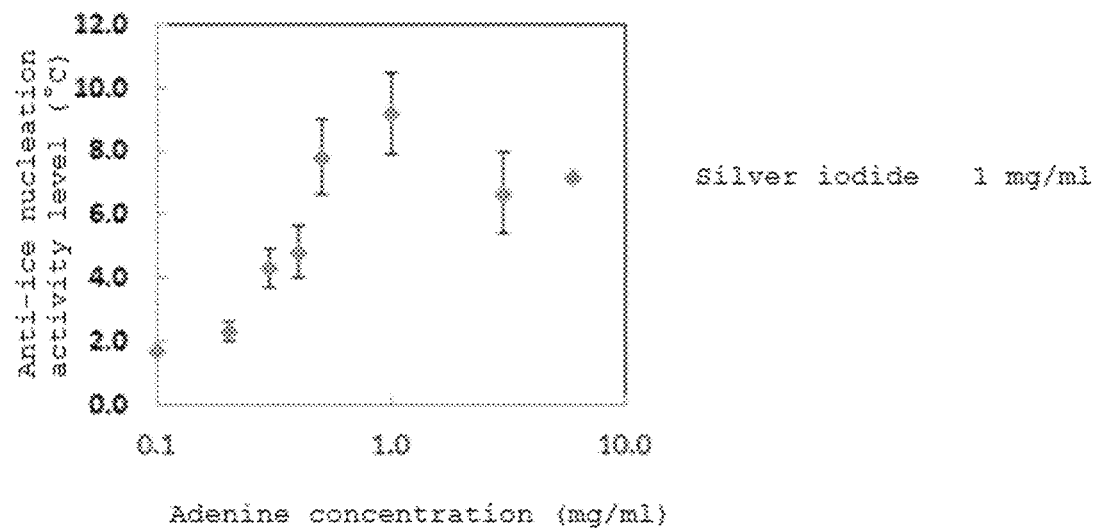
FIG. 1 is a graph showing the effect of the concentration of an anti-ice nucleation activator (adenine).

The anti-ice nucleation activator of the present invention comprises a purine base or a purine base-containing polymer. In this specification, the term "comprise/contain" encompasses the concepts of "comprise," "contain," "consist essentially of," and "consist of." The anti-ice nucleation activator means an agent that inhibits the occurrence of ice nucleation (an agent that promotes supercooling).

Purine Base

The purine base is not particularly limited, as long as it is a compound that has a purine skeleton. Generally, a purine base is a collective term for purines and purine compounds (derivatives) in which an arbitrary position or positions of the purine nucleus are substituted.

Examples of main purine bases include adenine, purine, guanine, hypoxanthine, xanthine, theobromine, caffeine, uric acid, isoguanine, theophylline, and the like.

In this specification, in addition to the adenine, purine, guanine, hypoxanthine, xanthine, theobromine, caffeine, uric acid, isoguanine, and theophylline mentioned above, the purine base encompasses compounds that have a chemical structure similar to these compounds (hereinafter may be referred to as "purine base derivatives"). Examples of purine base derivatives include compounds in which the hydrogen of the main purine bases is replaced by $C_{1-6}$ alkyl; compounds in which the hydrogen of purine bases is replaced by $C_{3-8}$ cycloalkyl; compounds in which the hydrogen or methyl of purine base compounds is replaced by aryl; and purine base derivatives, such as the heterocyclic compound disclosed in JP2000-63818A.

Of these, the purine base is preferably adenine, derivatives of adenine, caffeine, derivatives of caffeine, uric acid, and derivatives of uric acid; and more preferably adenine and derivatives of adenine.

The following are details of each group shown in this specification.

Examples of "alkyl" include, but are not particularly limited to, $C_{1-6}$ linear alkyl and $C_{3-6}$ branched alkyl groups. Specific examples include methyl, ethyl, n-propyl, isopropyl, n-butyl, isobutyl, s-butyl, t-butyl, n-pentyl, 2-methylbutyl, 1-methylbutyl, neopentyl, 1,2-dimethylpropyl, 1,1-dimethylpropyl, n-hexyl, 4-methylpentyl, 3-methylpentyl, 2-methylpentyl, 1-methylpentyl, 3,3-dimethylbutyl, 2,3-dimethylbutyl, 1,3-dimethylbutyl, 2,2-dimethylbutyl, 1,2-dimethylbutyl, 1,1-dimethylbutyl, 2-ethylbutyl, 1-ethylbutyl, 1,1,2-trimethylpropyl, 1-ethyl-2-methylpropyl, and the like. The alkyl is preferably $C_{1-6}$ linear alkyl, and more preferably methyl, ethyl, and n-butyl. The alkyl may have 1 to 6 substituents, such as halogen (e.g., fluorine, chlorine, bromine, and iodine), cyano, nitro, cycloalkyl (e.g., cyclopropyl, cyclobutyl, cyclopentyl, and cyclohexyl), and aryl (e.g., phenyl and naphthyl).

In this specification, "n-" means normal, "s-" means secondary (sec-), and "t-" means tertiary (tert-).

Examples of "cycloalkyl" include, but are not particularly limited to, $C_{3-8}$ cycloalkyl groups. Specific examples include cyclopropyl, cyclobutyl, cyclopentyl, cyclohexyl, cycloheptyl, cyclooctyl, and the like. The cycloalkyl is preferably $C_{3-7}$ cycloalkyl, more preferably $C_{5-7}$ cycloalkyl, and particularly preferably cyclohexyl. The cycloalkyl may have 1 to 6 substituents, such as halogen (e.g., fluorine, chlorine, bromine, and iodine), cyano, nitro, alkyl (e.g., $C_{1-6}$ alkyl), and aryl (e.g., phenyl and naphthyl).

Examples of "aryl" include, but are not particularly limited to, monocyclic aryl and aryl having two or more cyclic rings. Specific examples include phenyl, naphthyl, anthranyl, phenanthryl, and the like. The aryl is preferably monocyclic aryl or aryl having two cyclic rings, and more preferably phenyl. The aryl may have 1 to 6 substituents, such as halogen (e.g., fluorine, chlorine, bromine, and iodine), cyano, nitro, alkyl (e.g., $C_{1-6}$ alkyl), cycloalkyl (e.g., cyclopropyl, cyclobutyl, cyclopentyl, and cyclohexyl), and aryl (e.g., phenyl and naphthyl).

The purine bases may be used alone, or in a combination of two or more.

For purine bases, commercially available products may be used. If there are no commercially available products, purine bases may be produced in accordance with a known production method. For example, a compound in which the amino group ($-NH_2$) of adenine is converted into dimethylamino ($-NMe_2$) may be produced by reacting adenine with a methylating agent (e.g., methyl iodide).

Purine Base-Containing Polymer

The purine base-containing polymer refers to a polymer containing the purine base mentioned above as a repeating unit, and the purine base is present as side chains of the polymer. The number of purine bases per one molecule of the polymer is preferably 3 to 21, more preferably 6 to 18, and particularly preferably 9 to 15. The backbone of the polymer is not particularly limited, as long as the compound has a structure to which purine bases can bind. The purine base-containing polymer is preferably a polynucleotide, and more preferably deoxyribonucleic acid (DNA). The purine bases in the polymer are preferably adenine and derivatives of adenine; and it is particularly preferable that all of the purine bases in the polymer are adenine and derivatives of adenine. The purine base-containing polymer is particularly preferably polydeoxyadenylic acid.

The following describes the anti-ice nucleation activator of the present invention as a solid, unless otherwise specified; however, the anti-ice nucleation activator of the present invention is not limited to a solid. Specifically, the anti-ice nucleation activator of the present invention may be in the form of either a liquid or a solid. For example, if the anti-ice nucleation activator of the present invention is a solid, the solid may be used as an anti-ice nucleation activator by bringing the solid into contact with a biological material (e.g., food (e.g., seafood; plants, such as vegetables; edible meat, such as beef, pork, and chicken; protein-modified processed products, such as tofu and yogurt; and beverages) and biomaterials (e.g., cells (tissue) of plants or animals; human or animal blood; and human or animal organs or a portion thereof) so as to be dissolved in moisture of the biological material. If the anti-ice nucleation activator of the present invention is a liquid, the liquid may be used as an anti-ice nucleation activator for the biological material above by bringing the liquid into contact with the biological material (e.g., by spraying or dropping).

The anti-ice nucleation activator of the present invention may further comprise other components. Examples of other components include, but are not particularly limited to, known anti-ice nucleation activators (e.g., the anti-ice nucleation activator disclosed in JP2010-121052A), water, ethanol, and the like.

When the anti-ice nucleation activator of the present invention is formulated, the dosage form is not particularly limited. Examples of the dosage form include solutions, suspensions, emulsions, tablets, capsules, granules, powders, creams, ointment, and the like.

2. Antifreeze Liquid

The antifreeze liquid of the present invention comprises the purine base or purine base-containing polymer (anti-ice nucleation activator) described above, and water. The antifreeze liquid refers to a liquid that does not freeze at the freezing point (0° C.) of ice.

The amount of the purine base or purine base-containing polymer (anti-ice nucleation activator) contained in the antifreeze liquid is not particularly limited, and is usually within a range of 0.001 to 100 mg/mL, and preferably within a range of 0.1 to 10 mg/mL.

The water may be pure water or tap water. The water may contain an ice nucleation active substance.

Examples of ice nucleation active substances include, but are not limited to, *Pseudomonas* bacteria, silver iodide, fluoren-9-one, phenazine, metaldehyde, and the like. Of these, preferable ice nucleation active substances are *Pseudomonas syringae, Pseudomonas fluorescens*, and silver iodide.

A single kind, or a combination of two or more kinds of ice nucleation active substances, may be contained in the antifreeze liquid.

The amount of the ice nucleation active substance contained in the antifreeze liquid is not particularly limited, and is usually within a range of 0.001 to 100 mg/mL, and preferably within a range of 0.1 to 10 mg/mL.

The weight ratio of the anti-ice nucleation activator to the ice nucleation active substance in the antifreeze liquid is usually 1:10 to 1:200, preferably 1:10 to 1:100, and more preferably 1:10 to 1:20.

When a biological material (e.g., food (e.g., seafood; plants, such as vegetables; edible meat, such as beef, pork, and chicken; protein-modified processed products, such as tofu and yogurt; and beverages) and biomaterials (e.g., cells (tissue) of plants or animals; and human or animal organs or a portion thereof) is immersed in the antifreeze liquid of the present invention, or when the antifreeze liquid of the present invention is sprayed or dropped on the biological material, and cooling is performed, long-term, low-temperature preservation is possible usually at a temperature of 0° C. or lower, in particular within a temperature range of about 0° C. to −15° C., without the biological material being frozen (destroyed); or, even when it is frozen once, long-term, low-temperature preservation is possible since only fine ice nucleation is formed, which results in the occurrence of fine ice crystal formation.

3. Method for Improving the Anti-Ice Nucleation Activity of Biological Material

The method for improving the anti-ice nucleation activity of a biological material of the present invention comprises the step of bringing the above anti-ice nucleation activator (supercooling accelerator) or antifreeze liquid into contact with a biological material.

The biological materials are the same as the biological materials described above in sections 1 and 2.

Contact means that the anti-ice nucleation activator (supercooling accelerator), when it is a solid, is brought into contact with (uniformly sprinkled on) a biological material. The anti-ice nucleation activator is thereby dissolved in moisture of the biological material to exert the anti-ice nucleation activity. The anti-ice nucleation activator (supercooling accelerator) in a liquid form and the antifreeze liquid may be used as an anti-ice nucleation activator for the biological material by bringing the liquid into contact with (e.g., sprayed or dropped on) the biological material.

4. Method for Improving Anti-Ice Nucleation Activity of Food

The method for improving the anti-ice nucleation activity of food of the present invention comprises the step of bringing the anti-ice nucleation activator (supercooling accelerator) or antifreeze liquid into contact with food.

The food is the same as the food described above in sections 1 and 2. The meaning of contact is as described above in section 3.

5. Method for Preserving Biological Material

The method for preserving a biological material of the present invention comprises the step of bringing the anti-ice nucleation activator (supercooling accelerator) or antifreeze liquid into contact with a biological material.

The biological material is as described above in sections 1 and 2. The meaning of contact is as described above in section 3.

6. Method for Preserving Food

The method for preserving food of the present invention comprises the step of bringing the anti-ice nucleation activator (supercooling accelerator) or antifreeze liquid into contact with food.

The food is the same as the food described above in sections 1 and 2. The meaning of contact is as described above in section 3.

7. Application

The anti-ice nucleation activator (supercooling accelerator) of the present invention is widely applicable to food fields (e.g., quality preservatives for food and beverages (food preservatives and beverage preservatives)); medical fields (e.g., cell preservatives, blood preservatives, and organ preservatives); cosmetic fields; environmental fields (e.g., coating compositions and agents for preventing frost damage); and the like.

The anti-ice nucleation activator of the present invention may be added to a solution so as to be used as an antifreeze liquid. This antifreeze liquid may be used as a food preservation solution, a beverage preservation solution, a cell preservation solution, an organ preservation solution, an agent for preventing frost damage, a frost adhesion inhibitor, and the like.

The purine base-containing polymer (anti-ice nucleation activator) has excellent designability since the size of the polymer can be adjusted in consideration of the molecular weight of a target. The purine base-containing polymer (anti-ice nucleation activator) is particularly effective when used for a relatively large biological material, e.g., for organ preservation.

Food Preservative (Food Preservation Solution)

Examples of food for which the food preservative (food preservation solution) of the present invention can be used include, but are not limited to, perishable food, such as vegetables, fish, and meat (e.g., chicken, pork, and beef); processed food, such as juice, tofu, and Koya-tofu (freeze-dried tofu); and the like.

The use of the food preservative (food preservation solution) of the present invention enables preservation (retaining freshness). When the food is imported, exported, or transported, it is possible to convert the cryopreservation into supercooling preservation, which makes it possible to reduce electric power etc.

Cell Preservative (Cell Preservation Solution)

The cells for which the cell preservative (cell preservation solution) of the present invention can be used are not particularly limited, as long as they are cells of plants or animals. Examples include human cells, sperm, ovum, and the like.

The use of the cell preservative (cell preservation solution) of the present invention enables preservation without destroying cells.

Blood Preservative (Blood Preservation Solution)

The blood for which the blood preservative (blood preservation solution) of the present invention can be used is not particularly limited, as long as it is the blood of a human or an animal (excluding a human). Examples include whole blood, plasma, serum, and the like. The blood preservative (blood preservation solution) of the present invention may also be used for blood constituents, such as white blood cells, red blood cells, plasma, and thrombocytes.

Organ Preservative (Organ Preservation Solution)

The organs for which the organ preservative (organ preservation solution) of the present invention can be used are not particularly limited, as long as they are organs of a human or an animal (excluding a human), or a portion thereof.

The organ preservative (organ preservation solution) of the present invention may be used as a preservation solution for an organ taken at the time of an organ transplantation; a preservation solution for long-term preservation of an organ; and the like.

Agent for Preventing Frost Damage (Solution for Preventing Frost Damage)

The agent for preventing frost damage (solution for preventing frost damage) of the present invention can be used as a computer or car engine coolant; a frost adhesion inhibitor for freezers; an antifog agent for car windows; an agent for preventing dew condensation in tunnels; and the like.

The anti-ice nucleation activator or antifreeze liquid of the present invention may be used after mixing with a coating composition or the like. The target such as metal or resin coated with a coating composition containing the anti-ice nucleation activator of the present invention is prevented from frost damage or frost adhesion.

EXAMPLES

The present invention is described below in detail with reference to Examples. However, the present invention is not limited to these Examples.

Example 1

An aqueous solution was prepared by dissolving adenine (produced by Wako Pure Chemical Industries, Ltd.) as an anti-ice nucleation activator in ultra-pure water (Milli-Q™ ultra-pure water purification system, produced by Millipore Corp.) to a concentration of 1.0 mg/mL.

Examples 2 to 7

Solutions were prepared in a manner similar to that described in Example 1, except that the anti-ice nucleation activators shown in Table 1 were used in place of adenine.

Test Example 1

Evaluation of Anti-Ice Nucleation Active Performance (Supercooling Acceleration Performance) of Each Purine Base The anti-ice nucleation active performance (supercooling acceleration performance) of the anti-ice nucleation activators comprising the purine bases shown in Table 1 below (Examples 1 to 7) was evaluated according to the following method.

Nine hundred microliters of an aqueous solution was prepared by dissolving silver iodide (produced by Wako Pure Chemical Industries, Ltd.) in ultra-pure water to a silver iodide concentration of 1.0 mg/mL.

Each sample for evaluation was prepared by mixing 100 μL of the aqueous solutions of Examples 1 to 7 with 900 μL of the aqueous solution in which silver iodide was dissolved. A blank sample was prepared by mixing 100 μL of ultra-pure water with 900 μL of the aqueous solution in which silver iodide was dissolved.

Figure 3:
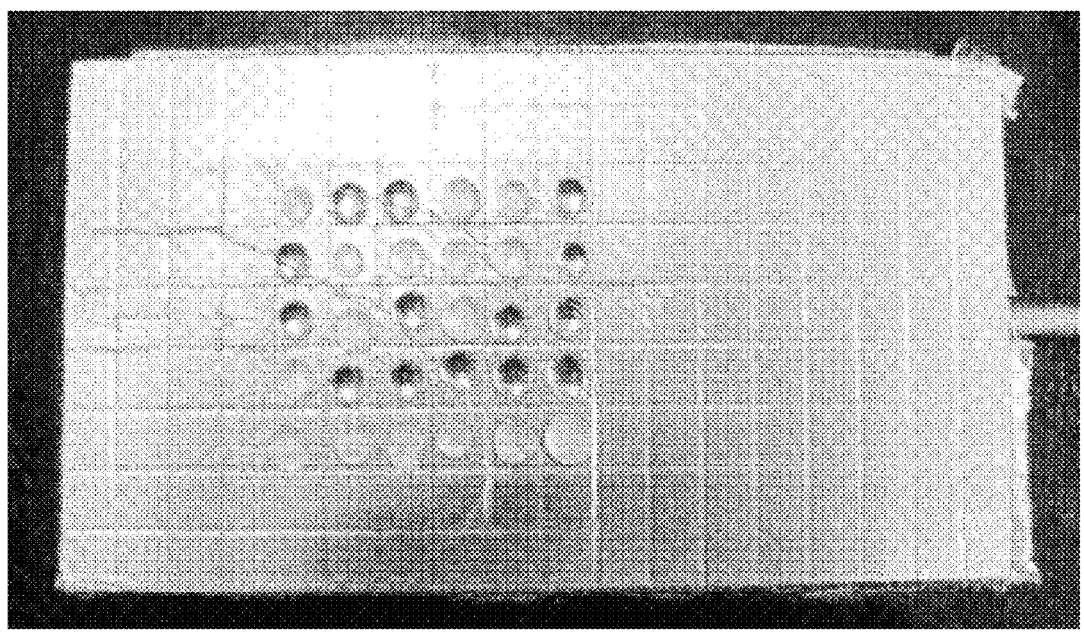
FIG. 3 is a photograph with regard to the droplet-freezing method of Vali.

The anti-ice nucleation active performance (supercooling acceleration performance) was measured by using the droplet-freezing method of Vali. More specifically, in accordance with the droplet-freezing method of Vali (FIG. 3), an aluminum film was placed on the copper plate of a cold plate chiller (CoolAce CCA-1000, Eyela), and the film was coated with a silicone oil suspension diluted with acetone and chloroform (a solution of acetone:chloroform=1:2). Then, each sample for evaluation or the blank sample was dropped (10 μL each) on 30 points of the surface, the temperature was decreased at a rate of 1.0° C./min, and the temperature at which 50% of the 30 droplets were frozen was considered to be $T_{50}$.

The droplet-freezing temperature of each sample was referred to as Sample$T_{50}$, and the droplet-freezing temperature of the blank sample was referred to as Blank$T_{50}$. Then, the anti-ice nucleation activity level $\Delta T_{50}$ (° C.) was calculated by the following formula:

Formula: $\Delta T_{50}$ (° C.)=Blank$T_{50}$−Sample$T_{50}$

Table 1 below shows the evaluation results of the anti-ice nucleation activators of Examples 1 to 7. The results are average values of the results of the test performed three times.

TABLE 1

|  | Purine base | Anti-ice nucleation activity level (° C.) |
| --- | --- | --- |
| Example 1 | Adenine | 9.2 |
| Example 2 | Guanine | 1.0 |
| Example 3 | Hypoxanthine | 2.1 |
| Example 4 | Theobromine | 1.2 |
| Example 5 | Caffeine | 1.3 |
| Example 6 | Uric acid | 1.8 |
| Example 7 | Theophylline | 2.0 |

Evaluation Results

The anti-ice nucleation activity level of all of the purine bases of Examples 1 to 7 was higher than 0, indicating that they exert the anti-ice nucleation activity.

Of these, adenine (Example 1) achieved the highest anti-ice nucleation activity level, showing the most excellent anti-ice nucleation activity. Next, Test Example 2 was conducted to analyze the effect of concentration of adenine.

Examples 8 to 14

Aqueous solutions were prepared by dissolving adenine in ultra-pure water to a concentration of 0.1 mg/mL (Example 8), 0.2 mg/mL (Example 9), 0.3 mg/mL (Example 10), 0.4 mg/mL (Example 11), 0.5 mg/mL (Example 12), 3.0 mg/mL (Example 13), and 6.0 mg/mL (Example 14).

Test Example 2

Effect of Purine Base Concentration

The effect of the concentration of the anti-ice nucleation activator (adenine) of Example 1 on the anti-ice nucleation activity was analyzed.

Nine hundred microliters of an aqueous solution was prepared by dissolving silver iodide in ultra-pure water to a silver iodide concentration of 1.0 mg/mL.

Each sample for evaluation was prepared by mixing 100 μL of the aqueous solutions of Examples 1 and 8 to 14 with 900 μL of the aqueous solution in which silver iodide was dissolved. A blank sample was prepared by mixing 100 μL of ultra-pure water with 900 μL of the aqueous solution in which silver iodide was dissolved.

The anti-ice nucleation active performance (supercooling acceleration performance) was measured by using the droplet-freezing method of Vali as described in Test Example 1. Table 2 and FIG. 1 show the evaluation results regarding the anti-ice nucleation activators of Examples 1 and 8 to 14. The results are average values of the results of the test performed three times.

TABLE 2

|  | Adenine concentration (mM) | Anti-ice nucleation activity level (° C.) |
| --- | --- | --- |
| Example 8 | 0.1 | 1.7 |
| Example 9 | 0.2 | 2.3 |
| Example 10 | 0.3 | 4.3 |
| Example 11 | 0.4 | 4.9 |
| Example 12 | 0.5 | 7.8 |
| Example 1 | 1.0 | 9.2 |
| Example 13 | 3.0 | 6.7 |
| Example 14 | 6.0 | 7.2 |

Evaluation Results

The anti-ice nucleation active performance was exerted at all of the adenine concentration levels within the range of 0.1 to 6.0 mg/mL. In particular, the anti-ice nucleation activity level at an adenine concentration of 1.0 mg/mL was most excellent (9.2° C.)

Test Example 3

Effect on Different Kind of Ice Nucleation Active Substance

A sample for evaluation of Example 1 was prepared in a manner similar to that described in Test Example 1, except that *Pseudomonas fluorescens*, which is the *Pseudomonas* bacterium, was used in place of silver iodide, which is an ice nucleation active substance. The anti-ice nucleation active performance (supercooling acceleration performance) was measured by using a test method similar to that described in Test Example 1. According to the results, the adenine-containing anti-ice nucleation activator also showed anti-ice nucleation active performance (1.0° C.) towards *Pseudomonas fluorescens* as well, in addition to silver iodide.

Test Example 4

Anti-Ice Nucleation Activity Test With Respect to Biological Material

Ten microliters of an aqueous solution in which the aqueous solution of the anti-ice nucleation activator of Example 1 (adenine) was diluted 10-fold with ultra-pure water (final concentration: 0.1 mg/mL) was added dropwise on a beef liver (1 mm (length)×1 mm (width)×1 mm (height)). As a blank sample, ultra-pure water was used.

The anti-ice nucleation active performance (supercooling acceleration performance) was measured by using a method similar to the droplet-freezing method of Vali described in Test Example 1. The results are average values of the results of the test performed three times.

The results revealed that the anti-ice nucleation activity level of the anti-ice nucleation activator (adenine) with respect to beef liver was 0.9° C.

Test Example 5

Anti-Ice Nucleation Activity Test With Respect to Biological Material

The anti-ice activity test was performed in a manner similar to that described in Test Example 4, except that the anti-ice nucleation activator of Example 5 (caffeine) was used in place of the anti-ice nucleation activator of Example 1 (adenine).

The results revealed that the anti-ice nucleation activity level of the anti-ice nucleation activator (caffeine) with respect to the beef liver was 0.7° C.

Examples 15 to 17

Aqueous solutions were prepared by dissolving polydeoxyadenylic acid having 6 bases (Example 15), 9 bases (Example 16), or 12 bases (Example 17) in a TE buffer solution to a concentration of 1.0 mg/mL.

Test Example 6

Effect of the Number of Bases in Purine Base

Regarding the adenine-containing polymer (polydeoxyadenylic acid), the effect of the number of bases on the anti-ice nucleation activity was analyzed.

Nine hundred microliters of an aqueous solution was prepared by dissolving silver iodide in ultra-pure water to a silver iodide concentration of 1.0 mg/mL.

Each sample for evaluation was prepared by mixing 100 μL of the aqueous solutions of Examples 15 to 17 with 900 μL of the aqueous solution in which silver iodide was dissolved. A blank sample was prepared by mixing 100 μL of ultra-pure water with 900 μL of the aqueous solution in which silver iodide was dissolved.

Figure 2:
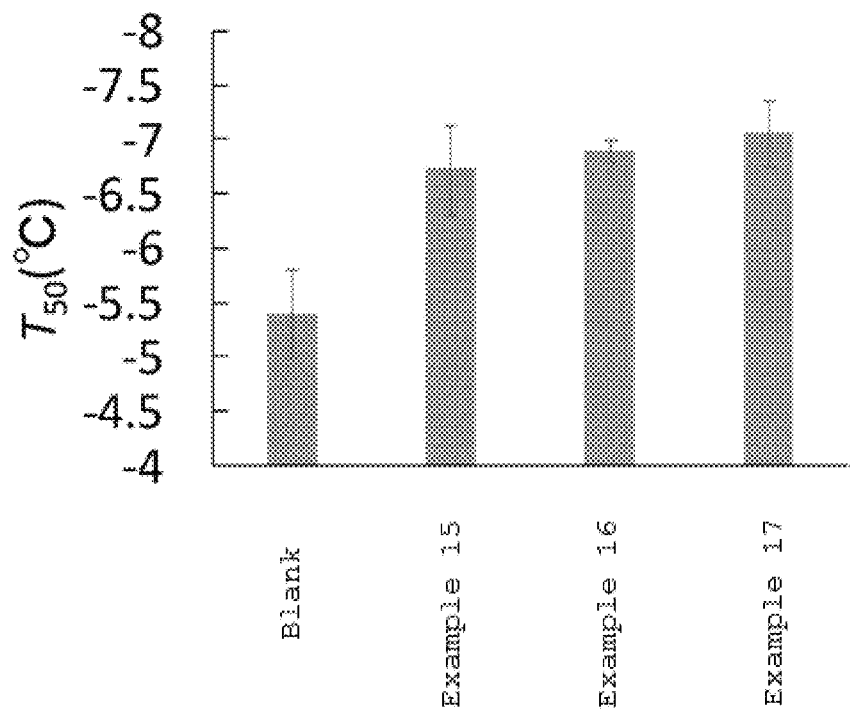
FIG. 2 is a graph showing the effect of the number of bases in an anti-ice nucleation activator (adenine).

The anti-ice nucleation active performance (supercooling acceleration performance) was measured by using the droplet-freezing method of Vali as described in Test Example 1. Table 3 and FIG. 2 show the evaluation results regarding the anti-ice nucleation activators of Examples 15 to 17. The results are average values of the results of the test performed three times.

TABLE 3

| | Number of adenine bases | Anti-ice nucleation activity level (° C.) |
|---|---|---|
| Example 15 | 6 | 1.26 |
| Example 16 | 9 | 1.43 |
| Example 17 | 12 | 1.60 |

Evaluation Results

The anti-ice nucleation activity level increased as the number of bases increased from 6 to 9, and then to 12 in polydeoxyadenylic acid. These results reveal that the ice nucleation activity can also be controlled even when a large ice nucleation active substance is used.

INDUSTRIAL APPLICABILITY

The anti-ice nucleation activator of the present invention is widely applicable to food fields (e.g., quality preservatives for frozen foods); environmental fields (e.g., agents for preventing frost damage); medical fields (e.g., cell preservatives, blood preservatives, and organ preservatives); and the like.

The invention claimed is:

1. A method for improving anti-ice nucleation activity of a biological material, the method comprising the steps of bringing an anti-ice nucleation activator comprising a purine base-containing polymer into contact with a biological material and cooling the biological material, wherein the purine base-containing polymer is a polydeoxyadenylic acid.

2. The method according claim 1, wherein the anti-ice nucleation activator is liquid.

3. The method according to claim 1, wherein the anti-ice nucleation activator further comprises water.

4. The method according to claim 1, wherein the biological material is cooled to 0° C. or lower in the cooling step.

* * * * *